United States Patent [19]
Ford et al.

[11] Patent Number: 4,597,911
[45] Date of Patent: Jul. 1, 1986

[54] PRODUCTION OF AMINO ALIPHATIC AND CYCLOALIPHATIC HYDROGEN SULFATES

[75] Inventors: Michael E. Ford, Center Valley; Thomas A. Johnson, Orefield, both of Pa.

[73] Assignee: Air Products and Chemicals, Inc., Allentown, Pa.

[21] Appl. No.: 561,616

[22] Filed: Dec. 14, 1983

[51] Int. Cl.$^4$ .................. C07C 141/02; C07C 141/12
[52] U.S. Cl. .......................................... 558/29; 558/30
[58] Field of Search ........................... 260/458 R, 457

[56] References Cited

U.S. PATENT DOCUMENTS

| | | | |
|---|---|---|---|
| 2,264,759 | 12/1941 | Jones | 260/458 R |
| 2,971,936 | 2/1961 | Dubien et al. | 260/458 R |
| 3,037,042 | 5/1962 | Laemmle | 260/458 R |
| 3,133,950 | 5/1964 | Pizzarello et al. | 260/458 R |
| 3,153,079 | 10/1964 | Forshaw | 260/458 R |
| 3,169,143 | 2/1965 | Gaulin et al. | 260/458 R |
| 3,194,826 | 7/1965 | Goldstein et al. | 260/458 R |
| 3,337,633 | 8/1967 | Schmitt et al. | 260/586 |
| 3,763,208 | 10/1973 | Sowerby | 260/458 R |
| 4,330,480 | 5/1982 | Hertel et al. | 260/458 R |

Primary Examiner—Nicky Chan
Attorney, Agent, or Firm—Russell L. Brewer; E. Eugene Innis; James C. Simmons

[57] ABSTRACT

Sulfuric acid esters of aminoalcohols are produced by reacting an amino alcohol with ammonium bisulfate or ammonium sulfate under acidic conditions. A representative sulfuric acid ester of an aliphatic amino alcohol is aminoethyl hydrogen sulfate.

5 Claims, No Drawings

PRODUCTION OF AMINO ALIPHATIC AND CYCLOALIPHATIC HYDROGEN SULFATES

TECHNICAL FIELD

This invention pertains to the synthesis of sulfuric acid esters of amino alcohols useful as intermediates in textiles, dyes, pharmaceuticals and polyamine synthesis.

BACKGROUND OF THE INVENTION

Typically, sulfuric acid esters of amino alcohols have been produced by reacting hydroxy aliphatic or cyclic alcohol amines with concentrated sulfuric acid or sulfur trioxide. Water is formed in the reaction with sulfuric acid, and, in order to drive the reaction to completion, the water is removed. Representative patents which illustrate the formation of sulfuric acid esters of amino alcohols by reaction of amino alcohols with sulfuric acid or sulfur trioxide and illustrate techniques for effecting removal of the water during the reaction for the amino aliphatic and cyclic hydrogen sulfate product are as follows:

U.S. Pat. No. 2,264,759 discloses the production of amino aliphatic hydrogen sulfates by reacting a hydroxy aliphatic amine with concentrated sulfuric acid in the presence of an organic solvent. Various solvents, e.g., hydrocarbons and chlorinated aromatic hydrocarbon solvents are added to the process to enhance the removal of water formed during the reaction. The addition of solvent to the reaction medium permitted distillation of water from the reaction medium at atmospheric pressure. Hydrogen sulfate salts of ethanolamine, triethanolamine, propanolamine and cyclohexylamine are shown.

U.S. Pat. No. 3,194,826 discloses a process for producing 2-aminoalkanol esters of sulfuric acid, particularly 2-aminoethyl sulfuric acid ester, by reacting monoethanolamine with sulfuric acid at temperatures from about 120°–200° C. Instead of removing all of the water from the reaction mixture prior to purification of the product, sufficient amount of water is retained in the reaction mixture to permit controlled crystallization of product.

U.S. Pat. No. 3,133,950 discloses a process for reacting an alkanolamine with sulfuric acid in the presence of a small amount of a cationic surface active agent. In an effort to force the reaction to completion, the reaction is carried out in the presence of an inert volatile solvent which is capable of forming azeotrope with water. Representative cationic surface active agents include long chain quaternary ammonium compounds, fatty acid diamine condensates and fatty acid carbamides.

U.S. Pat. No. 4,330,480; U.S. Pat. No. 3,153,079 and U.S. Pat. No. 3,194,826 show variations on the above themes in the manufacture of aminoalkyl esters of sulfuric acid.

U.S. Pat. Nos. 3,169,143, 3,763,208 and 3,337,633 disclose the preparation of sulfuric acid esters of aminoalkanols, particularly 2-aminoethyl esters of sulfuric acid, by reacting an alkanolamine with sulfur trioxide. U.S. Pat. No. 3,337,633 shows the preparation of sulfuric acid esters of ethoxy linear saturated secondary alcohols by reacting an ethoxy substituted alcohol with sulfamic acid.

SUMMARY OF THE INVENTION

This invention pertains to an improvement in a process for producing amino aliphatic and cyclic esters of sulfuric acid by effecting reaction between a sulfate radical providing compound with an amino alcohol. The improvement in the process resides in utilizing ammonium sulfate or ammonium bisulfate as the sulfate radical providing compound and carrying out the reaction under acidic conditions. This process is particularly advantageous in the preparation of 2-aminoethyl hydrogen sulfate by the reaction of monoethanolamine with ammonium bisulfate.

A major advantage of the process is that the bisulfate reactant employed, in particular, is a by-product of many processes, e.g., polyamine synthesis via the reaction of an aminoalkyl hydrogen sulfate with sodium hydroxide as shown in U.S. Pat. No. 2,318,730.

DETAILED DESCRIPTION OF THE INVENTION

By the process of this invention, hydroxyaliphatic amines are converted to sulfuric acid esters. Suitable hydroxyaliphatic and hydroxy cyclic amines for carrying out the process include $C_2$–$C_8$ alkanolamines, such as, diethanolamine, triethanolamine, 3-aminopropyl alcohol, 3-aminobutyl alcohol; substituted derivatives of alkanolamines, such as, 2-methyl ethanolamine, dimethyl ethanolamine, N-isopropylethanolamine, N-methylethanolamine and N-acetyl monoethanolamine; $C_{6-10}$ cyclic and cycloalkyl systems such as 2-aminocyclohexyl alcohol and aminoethyl cyclohexanol; and hydroxyethyl urea and hydroxyethyl carbamide.

The sulfation of the hydroxyaliphatic and cyclic amines is carried out under conditions sufficient to effect coupling of the bisulfate radical with the hydroxy group on the amino alcohol. To do that, reaction temperature will range from about 100°–200° C., and the pressure will range from vacuum to superatmospheric pressures, e.g. 100 atmospheres. Generally, atmospheric pressure is used. Similarly in the sulfuric acid esterification process, water is produced as a by-product and must be removed during the reaction in order to drive the reaction to completion. Numerous water insoluble solvents which azeotrope with water can be utilized to remove the water from the system. Examples of suitable organic solvents include hydrocarbons, such as benzene, xylene, toluene, solvent naphtha, gasoline, isooctane, cyclohexane, and others. Chlorinated aromatic solvents are also suited, and these include chlorobenzenes, orthodichlorobenzene, mixed chlorotoluenes, methylene chloride and the like. Representative solvents are shown in U.S. Pat. Nos. 2,264,759 and 4,330,480; these references are incorporated by reference.

The reaction between the hydroxyaliphatic amines or cyclic amines and ammonium sulfate or ammonium bisulfate should be conducted under acidic conditions. By that it is meant the system should contain sufficient acid for neutralizing or capturing by-product ammonia as it is formed during the reaction. Therefore, in reaction mixtures where ammonium bisulfate is used as the reactant, the molar ratio of ammonium bisulfate to hydroxyaliphatic or cyclic amine should be at least 2:1, the extra mole of ammonium bisulfate being used to capture by-product ammonia. Normally, a ratio of 4–10:1 is used. When less than 2 moles of ammonium bisulfate to amine are used, conversion of the amine to the sulfate ester normally will cease when the reaction conditions move to a basic condition. Although conversions can be enhanced when the conditions are slightly basic by increasing temperature, e.g. to a level of about 200° C. to 260° C., the rate of conversion to the sulfate ester of the amino alcohol is slow and extensive charring of the product or reaction mixture can occur.

At the conclusion of the reaction, the product sulfate ester of the amino alcohol is recovered by conventional techniques. Typically, this involves distilling the water from the reaction medium and then cooling the reaction mixture and effecting crystallization of the product. As noted in the prior art, by appropriate application of heat and vacuum and by retaining sufficient water in the reaction mixture, one can achieve controlled crystallization of the product. Once the product is crystallized, then simple recovery techniques such as centrifugation or filtration can be used to separate the product from the suspension. Hydrolysis of the product can be minimized during the crystallization of product by including, in dilute concentration, e.g., 0.1–1% by weight based upon the weight of the water present in the system, of a water soluble salt of a weak acid. Examples of such salts include sodium acetate, sodium propionate, sodium dihydrogen phosphate and the corresponding potassium counterparts. Other salts and techniques for reducing hydrolysis are disclosed in U.S. Pat. No. 3,037,042 and are incorporated by reference.

The following examples are provided to illustrate embodiments of the invention.

EXAMPLE 1

A series of runs were conducted to produce 2-aminoethyl hydrogen sulfate by the reaction of monoethanolamine with ammonium bisulfate and ammonium sulfate. The following general procedure was utilized in producing 2-aminoethyl hydrogen sulfate.

A preselected quantity of ammonium bisulfate or ammonium sulfate, was charged to a 250 ml 3-necked round bottom flask, fitted with a water-cooled condenser, and thermometer. Then, a preselected quantity of solvent and monoethanolamine were charged to the flask and the flask sealed. At this point the contents were slowly heated under constant agitation, to avoid bumping the reaction mixture, to reflux temperature. The contents were then held at reflux temperature for a period of time and the reaction terminated.

The product, 2-aminoethyl hydrogen sulfate, was recovered from the reaction mixture by crystallizing it from the solution and then drying the resulting solid in a vacuum oven. The samples were analyzed by utilizing a 60 MHz proton NMR on a Hitachi Perkin-Elmer R-24B high resolution NMR spectrometer and by a carbon-13 NMR technique on a Bruker WP-200FT NMR spectrometer.

Table 1, which follows, provides results for the reaction of either ammonium bisulfate or ammonium sulfate with monoethanolamine at various feed ratios, conditions etc., to produce 2-aminoethyl hydrogen sulfate. The quantities of ammonium sulfate or ammonium bisulfate and monoethanolamine (MELA) charged to the reactor, feed ratio, solvent, reaction time as indicated by various samples taken within the run, temperature (°C.), percent conversion, percent selectivity and yields are reported.

The percent conversion is expressed in units of mole percent by proton nuclear magnetic resonance analysis of the reaction mixture. Unless otherwise noted in the entry for selectivity, only 2-aminoethyl hydrogen sulfate (AES) and monoethanolammonium sulfate were present at the end of each reaction (by proton and carbon NMR). Owing to the rapidity of analysis, proton NMR was routinely used to characterize samples of reaction mixtures. The proton spectrum of AES exhibits triplets at 4.28 ppm ($CH_2$—O; J=6 Hz) and 3.32 ppm ($CH_2$—O; J=6 Hz), while that of monoethanolammonium sulfate exhibits triplets at 3.78 ppm ($CH_2$—O; J=6 Hz) and 3.12 ppm ($CH_2$—O; J=6 Hz). Signals for the methylene groups adjacent to the amino functionality of monoethanolammonium sulfate and AES were believed not to be sufficiently resolved by 60 MHz proton NMR to permit accurate quantitation. Therefore, conversion of monoethanolamine to AES was judged by comparison of the integrated signals areas for the methylene groups adjacent to the oxygen functionality of AES and monoethanolammonium sulfate. Conversion is expressed by:

$$\text{Conversion} = \frac{\text{Area}_{AES}}{\text{Area}_{AES} + \text{Area}_{monoethanolammonium\ sulfate}} \times 100\%$$

The percent selectivity was evaluated in units of mole percent by carbon NMR. Unless otherwise noted, only AES and monoethanolammonium sulfate were present at the end of each reaction; no by-products could be detected.

Yield is expressed in units of mole percent as the product of conversion times selectivity.

TABLE 1

| Run | Ammonium Bisulfate (gm) | MELA (gm) | Feed Ratio (molar) | Solvent (ml) | Time (hr) | Temp (°C.) | Conversion (%) | Selectivity (%) | Yield (%) |
|---|---|---|---|---|---|---|---|---|---|
| 1A | 46.0 | 12.0 | 2/1 | Diphenyl ether(60) | 1.0 | 100$^f$ | 28 | 100 | 28 |
| B | | | | | 2.0 | 100$^f$ | 31 | 100 | 31 |
| C | | | | | 4.0 | 100$^f$ | 32 | 100 | 32 |
| 2A | 46.0 | 12.0 | 2/1 | Diphenyl ether(60) | 1.0 | 150$^f$ | 36 | 100 | 36 |
| B | | | | | 2.0 | 150$^f$ | 38 | 100 | 38 |
| 3A | 46.0 | 12.0 | 2/1 | Diphenyl ether(60) | 1.0 | 220$^f$ | 43 | 100 | 43 |
| B | | | | | 4.0 | 220$^f$ | 45 | 100 | 45 |
| 4A | 46.0 | 12.0 | 2/1 | Diphenyl ether(60) | 1.5 | 260$^g$ | 52 | 100 | 52 |
| B | | | | | 2.0 | 260$^g$ | 57 | 85–90 | 48–51 |
| 5 | 23.0 | 6.0 | 2/1 | o-Dichlorobenzene(30) | 1.5 | 190 | 52 | 100 | 52 |
| 6A | 96.0 | 12.0 | 4/1 | Diphenyl ether(60) | 1.0 | 100$^f$ | 50 | 100 | 50 |
| B | | | | | 2.0 | 100$^f$ | 52 | 100 | 52 |
| C | | | | | 4.0 | 100$^f$ | 54 | 100 | 54 |
| 7A | 46.0 | 12.0 | 2/1 | Toluene(85) | 1 | 110 | 46 | 100 | 46 |
| B | | | | | 3 | 110 | 47 | 100 | 47 |
| C | | | | | 8 | 110 | 69 | 100 | 69 |
| D | | | | | 24 | 110 | 99 | 100 | 99 |
| 8A | 46.0 | 12.0 | 2/1 | Nonane(85) | 1 | 150 | 56 | 100 | 56 |

TABLE 1-continued

| Run | Ammonium Bisulfate (gm) | MELA (gm) | Feed Ratio (molar) | Solvent (ml) | Time (hr) | Temp (°C.) | Conversion (%) | Selectivity (%) | Yield (%) |
|---|---|---|---|---|---|---|---|---|---|
| B | | | | | 2 | 110 | 71 | 100 | 71 |
| C | | | | | 8 | 110 | 95 | 100 | 95 |
| 9A | 46.0 | 12.0 | 2/1 | Mesityl- | 1 | 167 | 99 | 100 | 99 |
| B | | | | ene(85) | 2 | 167 | 99 | 100 | 99 |
| C | | | | | 9 | 167 | 99 | 100 | 99 |
| 10A | 46.0 | 12.0 | 2/1 | 2-Ethyl- | 1 | 185 | 99 | 100 | 99 |
| B | | | | hexanol | 2 | 185 | 99 | 100 | 99 |
| C | | | | (85) | 9 | 185 | 99 | 100 | 99 |
| 11A | 57.5 | 10.0 | 3/1 | Mesityl- | 1 | 167 | 99 | 100 | 99 |
| B | | | | ene(125) | 2 | 167 | 99 | 100 | 99 |
| 12A | 92.0 | 12.0 | 4/1 | Toluene | 1 | 110 | 61 | 100 | 61 |
| B | | | | (130) | 3 | 110 | 68 | 100 | 68 |
| | | | | | 8 | 110 | 78 | 100 | 78 |
| | | | | | 24 | 110 | 96 | 100 | 96 |
| 13A | 92.0 | 12.0 | 4/1 | Nonane | 1 | 150 | 73 | 100 | 73 |
| B | | | | (130) | 3 | 110 | 81 | 100 | 81 |
| | | | | | 8 | 110 | 91 | 100 | 91 |
| | | | | | 24 | 110 | 99 | 100 | 99 |
| 14A | 55.0 | 7.5 | 3.9/1 | 4-Chloro- | 1 | 161 | 99 | 100 | 99 |
| | | | | toluene (125) | 2 | 161 | 99 | 100 | 99 |
| 15A | 55.0 | 7.5 | 3.9/1 | Mesitylene | 1 | 167 | 99 | 100 | 99 |
| B | | | | (125) | 2 | 167 | 99 | 100 | 99 |
| 16A | 115.1 | 7.5 | 8/1 | Nonane | 1 | 150 | 88 | 100 | 88 |
| B | | | | (130) | 2 | 150 | 94 | 100 | 94 |
| *17A | 28.75 | 3.8 | 4/1 | No solvent | 1 | 165 | 69 | 100 | 69 |
| B | | | | nitrogen purge | 2.5 | 165 | 87 | 100 | 87 |
| 18A | 34.5 | 12.0 | 1.5/1 | Mesitylene (85) | 1.5 | 167 | 69 | 60–65 | 41–45 |
| | | | | | 2 | 167 | 73 | 60–65 | 44–47 |
| 19 | Ammonium Sulfate 66.0 | 30.5 | 1/1 | None | — | 225° C. | 67.5 | 17.1 | 11.6 |

$f$Reaction mixture thermostated at this temperature
$g$Reflux temperature
*A nitrogen purge was used in Runs 17A & B to enhance water removal.

The data in Table 1 shows that good conversion and selectivity can be achieved in the reaction of monoethanolamine with ammonium bisulfate to form the sulfate ester. The data shows that if the initial mole ratio of ammonium bisulfate/monoethanolamine is less than 2/1, conversion of monoethanolamine is incomplete, even with azeotropic removal of coproduct water (Compare Run 18A & B against Run 9A & B). It is believed incomplete conversion results from failure to maintain an acidic reaction medium for effecting absorption of product ammonia.

When a stoichiometric 2/1 molar ratio of ammonium bisulfate to monoethanolamine is used, relatively long times are required in order to obtain essentially complete conversion of monoethanolamine to AES at reaction temperatures of 150° C. or less (see Runs 7 and 8). Use of higher molar ratios of ammonium bisulfate to monoethanolamine (e.g. 4/1) generally enhances the rate of conversion of monoethanolamine to AES at these same low temperatures (Compare Runs 8A, 12 & 13A, B, and C). However, higher temperatures also enhance conversion at the same molar ratios presumably by enhancing removal of water from mixtures of ammonium bisulfate and monoethanolamine. Selective production of AES also is obtained. (See Runs 9–11, 14 and 15). Finally, the rate of conversion of monoethanolamine to AES may also be enhanced by removal of by-product water with a nitrogen purge (see Run 17). Conversion of monoethanolamine to the sulfate ester is difficult (Run 19) when ammonium sulfate is used as a reactant even under forcing conditions, e.g. temperatures higher than 200° C. Selectivities were also poor as compared to those runs where ammonium bisulfate was the reactant.

EXAMPLE 2

The procedure of Example 1 was repeated except that N-acetylmonoethanolamine (NAEA) was used in place of monoethanolamine. Table 2 shows the results for a variety of runs carried out with ammonium bisulfate and ammonium sulfate as the reactant. Surprisingly, the reactants cleave to form aminoethyl sulfate (AES) as the product as opposed to another form of sulfate ester. Run 6 resulted in no AES, presumably due to the lack of acidic conditions. On the other hand, the reaction proceded favorably where reaction conditions were acidic.

| Run | Ammonium Bisulfate (gm) | NAEA (gm) | Feed Ratio (molar) | Solvent (ml) | Time (hr) | Temp (°C.) | Conversion (%) | Selectivity (%) | Yield (%) |
|---|---|---|---|---|---|---|---|---|---|
| 1A | 46.0 | 10.4 | 4/1 | Mesitylene | 0.5 | 168 | 47.4 | 100 | 47.4 |
| B | | | | (100) | 1.0 | 168 | 72.0 | 100 | 72.0 |
| C | | | | | 1.5 | 168 | 79.5 | 100 | 79.5 |
| D | | | | | 2.0 | 168 | 82.3 | 100 | 82.3 |
| 2A | 46.0 | 10.4 | 4/1 | Decane | 0.5 | 180 | 41.7 | 100 | 41.7 |
| B | | | | (100) | 1.0 | 180 | 77.5 | 100 | 77.5 |
| C | | | | | 1.5 | 180 | 88.3 | 100 | 88.3 |
| D | | | | | 2.0 | 180 | 91.9 | 100 | 91.9 |
| 3A | 46.0 | 5.2 | 8/1 | Mesitylene | 0.5 | 168 | 62.4 | 100 | 62.4 |

-continued

| Run | Ammonium Bisulfate (gm) | NAEA (gm) | Feed Ratio (molar) | Solvent (ml) | Time (hr) | Temp (°C.) | Conversion (%) | Selectivity (%) | Yield (%) |
|---|---|---|---|---|---|---|---|---|---|
| B | | | | (100) | 1.0 | 168 | 77.5 | 100 | 83.0 |
| C | | | | | 1.5 | 168 | 88.3 | 100 | 90.4 |
| D | | | | | 2.0 | 168 | 91.9 | 100 | 95.7 |
| 4A | 46.0 | 5.2 | 8/1 | Decane | 0.5 | 180 | 66.6 | 100 | 66.6 |
| B | | | | (100) | 1.0 | 180 | 72.2 | 100 | 72.2 |
| C | | | | | 1.5 | 180 | 81.7 | 100 | 81.7 |
| D | | | | | 2.0 | 180 | 89.0 | 100 | 89.0 |
| 5A | 34.5 | 20.6 | 1.5/1.0 | Mesitylene | 0.25 | 168 | 2 | 100 | 2 |
| B | | | | (100) | 1.0 | 168 | 7 | 100 | 7 |
| C | | | | | 1.5 | 168 | 12 | 100 | 12 |
| D | | | | | 2.0 | 168 | 57 | 100 | 57 |
| 6A | Ammonium Sulfate 52.8 | (10.3) | 4/1 | Mesitylene | 0.25 | 168 | 0 | 100$^j$ | 0 |
| B | | | | (125) | 1.0 | 168 | 0 | 100$^j$ | 0 |
| C | | | | | 1.5 | 168 | 0 | 100$^j$ | 0 |
| D | | | | | 2.0 | 168 | 0 | 100$^j$ | 0 |

$^j$No AES detected

What is claimed is:

1. In a process for producing a hydrogen sulfate ester by reacting an amino compound selected from the group consisting of $C_{2-8}$ alkanolamines, hydroxy ethyl urea, aminocyclohexanol, aminoethylcyclohexanol, and N-acetyl monoethanolamine with a sulfate radical providing compound, the improvement which comprises utilizing ammonium bisulfate as the sulfate providing radical, and carrying out the reaction at a temperature from 100°–200° C., and maintaining a mole ratio of ammonium bisulfate to said amino compound of 2–10:1.

2. The process of claim 1 wherein the reaction is carried out in the presence of an organic water insoluble solvent which is capable of forming an azeotrope with water at the reaction temperature.

3. The process of claim 2 wherein said alkanolamine is monoethanolamine.

4. The process of claim 2 wherein said amino compound is N-acetyl monoethanolamine.

5. The process of claim 2 wherein said molar ratios of ammonium bisulfate to said amino compound is maintained from 4–10:1.

* * * * *